(12) United States Patent
Kreider et al.

(10) Patent No.: US 12,097,286 B1
(45) Date of Patent: Sep. 24, 2024

(54) ENHANCED CONFECTIONERY

(71) Applicant: Albatros Holdings LLC, Broomfield, CO (US)

(72) Inventors: Erik Lawrence Kreider, Lafayette, CO (US); Bryan E. Burke, Broomfield, CO (US)

( * ) Notice: Subject to any disclaimer, the term of this patent is extended or adjusted under 35 U.S.C. 154(b) by 0 days.

(21) Appl. No.: 18/403,960

(22) Filed: Jan. 4, 2024

(51) Int. Cl.
*A61K 9/00* (2006.01)
*A23G 3/34* (2006.01)
*A23G 3/36* (2006.01)
*A23G 3/54* (2006.01)
*A61K 31/00* (2006.01)

(52) U.S. Cl.
CPC .......... *A61K 9/0056* (2013.01); *A23G 3/0063* (2013.01); *A23G 3/364* (2013.01); *A23G 3/54* (2013.01); *A61K 9/006* (2013.01); *A61K 31/658* (2023.05)

(58) Field of Classification Search
CPC .... A61K 9/0056; A61K 9/006; A61K 31/658; A23G 3/0063; A23G 3/364; A23G 3/54
See application file for complete search history.

(56) References Cited

U.S. PATENT DOCUMENTS

| 10,555,906 | B2 * | 2/2020 | Sacks | A61K 31/352 |
| 2019/0183141 | A1 * | 6/2019 | Hesson | A23G 3/0089 |

* cited by examiner

*Primary Examiner* — Deborah D Carr
(74) *Attorney, Agent, or Firm* — MP Patents, LLC

(57) ABSTRACT

A confectionery method includes dissolving at least one active ingredient in a volatile vehicle to form a solution, applying the solution to a substrate and evaporating the volatile vehicle to leave the at least one active ingredient applied to the substrate. A confection includes an edible substrate and at least one active ingredient provided to the edible substrate.

23 Claims, 4 Drawing Sheets

ENHANCED CONFECTIONERY

SUMMARY

The disclosure describes a confectionery method. The method includes dissolving at least one active ingredient in a volatile vehicle to form a solution, applying the solution to a substrate and evaporating the volatile vehicle to leave the at least one active ingredient applied to the substrate.

The disclosure also describes a confection resulting from the methods disclosed herein. The confection includes an edible substrate and at least one active ingredient provided to the edible substrate.

BRIEF DESCRIPTION OF THE FIGURES

The summary above, as well as the following detailed description of illustrative embodiments, is better understood when read in conjunction with the appended figures. For the purpose of illustrating the present disclosure, example constructions of the disclosure are shown in the figures. However, the present disclosure is not limited to specific methods and instrumentalities disclosed herein. Moreover, those of skill in the art will understand that the figures are not to scale. Wherever possible, like elements have been indicated by identical numbers.

Embodiments of the present disclosure will now be described, by way of example only, with reference to the following figures wherein.

DETAILED DESCRIPTION

The following detailed description illustrates embodiments of the present disclosure and manners by which they can be implemented. Although the best mode of carrying out the disclosure has been described, those having skill in the art would recognize that other embodiments for carrying out or practicing the present disclosure are also possible.

It should be noted that the terms "first", "second", and the like, herein do not denote any order, quantity, or importance, but rather are used to distinguish one element from another. Further, the terms "a" and "an" herein do not denote a limitation of quantity, but rather denote the presence of at least one of the referenced item.

Historically, it has not been possible to provide certain confections with active ingredients of interest because many such active ingredients are susceptible to temperature instability during confection production techniques using heat and/or the confection itself is susceptible to degradation by water or water-containing vehicles. For example, popping candy relies on the presence of microscopic bubbles of high-pressure carbon dioxide gas encapsulated within the sugar confection matrix and pops when the bubble envelope is dissolved by saliva in the mouth. The presence of water in a vehicle used to apply an active ingredient prematurely dissolves the bubble envelope and degrades the popping effect. Further, many known vehicles which might be used to dissolve active ingredients and apply to the confection post-production are toxic and/or cannot be completely removed before consumption of the confection.

Disclosed methods employ vehicles applicable to confections which do not degrade the confection or any underlying sugar structure. Further, disclosed methods employ vehicles which are non-toxic and/or are easily removable from the confection. Active ingredients may be dissolved in disclosed vehicles and applied to confections post-production so that the active ingredients are not damaged by the production of an underlying confection substrate. Such dosing with active ingredients can be achieved volumetrically in a reliable and consistent manner with even distribution.

Additional aspects, advantages, features and objects of the disclosure will be made apparent from the figures and the detailed description of the illustrative embodiments construed in conjunction with the appended claims that follow. It will be appreciated that features of the disclosure are susceptible to being combined in various combinations without departing from the scope of the disclosure as defined by the appended claims.

Figure 1:
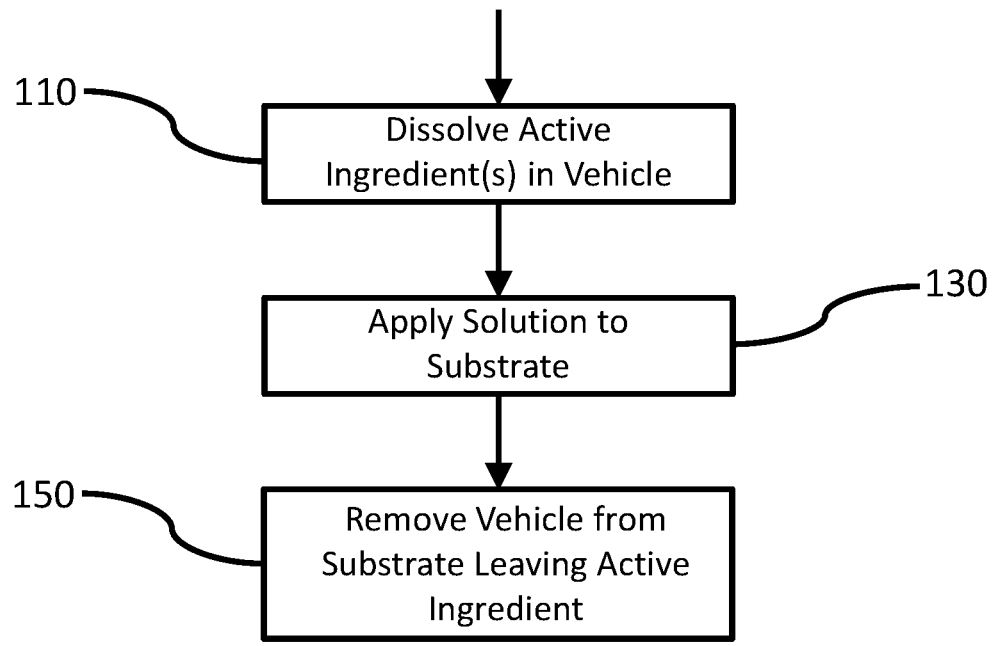
FIG. 1 illustrates an example confectionery method.

FIG. 1 illustrates actions of an example confectionery method, in accordance with an embodiment of the disclosure. The method is depicted as a collection of actions in a logical flow diagram, which represents a sequence of actions. The method includes dissolving at least one active ingredient in a volatile vehicle to form a solution at 110, applying the solution to a substrate at 130 and removing the volatile vehicle, for example by evaporating, at 150 to leave the active ingredient applied to the substrate.

In an example, the at least one active ingredient may be dissolved in a solvent vehicle which does not dissolve sugar or in which sugar is insoluble. In another example, the at least one active ingredient may be dissolved in a vehicle which is anhydrous.

Vehicles suitable for use in association with disclosed methods may have a boiling point above room temperature but below the melting point of the chosen substrate at atmospheric pressure. For example, suitable vehicles have boiling points less than or equal to 78° C. at atmospheric pressure and a vapor pressure of about 55 mm Hg. Suitable vehicles may also be subject to USP purity standards, be non-toxic and/or leave no undesirable residue.

Vehicles suitable for use in association with disclosed methods may have low vapor pressure at room temperature, may be a polar solvent which is miscible with a variety of non-polar solvents, may be easily removable from a substrate by vacuum or lyophilization and may have an innocuous toxicity profile.

For example, the at least one active ingredient may be dissolved in a pure ethanol vehicle which may be a suitable solvent for dissolving any of a variety of active ingredients of interest. Distillation, a common technique for producing ethanol is limited to a yield of only 95% ethanol and 5% water due to the mixture eutectic point. Cracking ethanol from petroleum has generally not been economical. In an example, the pure ethanol disclosed herein may be economically produced by size exclusion filtration. The low vapor pressure of pure ethanol may facilitate liquid application to substrates for even application across the substate matrix. Between room temperature and 90° C., the vapor pressure of ethanol increases by an order of magnitude so that it is easily removed from a substrate to which it has been applied. 90° C. is well below the boiling point of water and about half the melting point of sugars and hard candy. As a polar solvent, pure ethanol is miscible with many non-polar solvents and is eminently suitable for dissolving a wide range of active ingredients. No known solvents are as innocuous as pure ethanol.

Other example vehicles into which one or more active ingredients may be dissolved include but are not limited to methanol, isopropanol, pentane, hexane, heptane, cyclohexane, benzene, acetone, ethyl acetate and butanone. Some example vehicles used for dissolving active ingredients prior to application to an edible substrate will require removal to a degree sufficient to pass contamination standards.

The at least one active ingredient dissolved in the vehicle may be configured for buccal and/or sublingual delivery which may support consistent dosing of active ingredients, bioavailability and biochemical effect while avoiding portal vein, first-pass liver metabolism and/or gut bioavailability complications.

Example active ingredients include but are not limited to one or more of, nicotine, benzocaine, caffeine, taurine and natural and/or artificial flavors. In an alternative, the at least one active ingredient may include one or more of pain drugs such as fentanyl or methadone. In another alternative, the at least one active ingredient may include one or more of methylenedioxyamphetamine (MDA), 3,4-Methylenedioxymethamphetamine (MDMA), ketamine, psilocin, and psilocybin. In yet another alternative, the at least one active ingredient may include one or more of a hemp extract, a *cannabis* distillate, a *cannabis* extract, a cannabinoid such as delta-9-tetrahydrocannabinol, cannabidiol or cannabigerol.

The solution may be applied to the substrate superficially and/or coat the substrate as a thin film or microcrystals such that the solution and/or the at least one active ingredient effectively do not penetrate the substrate.

Applying the solution to the substrate may further include applying to an edible substrate. For example, the solution may be applied to a substrate including at least one water-sensitive component or ingredient such as one which is soluble in water. In a further example, the solution may be applied to a substrate including a sugar such as a candy or pastry substrate. The solution may be applied to a substrate including a spun sugar or bubbles of carbon dioxide such as are found in popping candy. The solution may be applied to a substrate including chocolate, hard candy, gum or a breath freshener.

The solution including the active ingredient or ingredients may be applied according to any of a variety of volumetric dispensing methods. For example, the solution may be applied to the substrate by depositing droplets thereof onto the substrate, immersing the substrate in the solution, spraying the solution onto the substrate and/or atomizing the solution such as by creating a fine mist and spraying onto the substrate. As further examples, the solution may be applied using a hand-held spray bottle, a pump spray bottle or a pressure spray head or airbrush. As still further examples, the solution may be applied as droplets from a dropper bottle, pipette or Pipetman™. Further still, the solution may be applied via droplets into single serving packages, whereupon the vehicle is completely evaporated prior to sealing an associated container.

The vehicle may be removed from the substrate according to any of a variety of evaporation techniques which will not melt or otherwise degrade the substrate. Example techniques include but are not limited to application of heat or vacuum to the coated substrate, use of a dry gas jet and/or lyophilization. In a further example, the coated substrate may be conveyed through a heat tube to dry the ethanol.

Disclosed methods may be suitable for providing any of a variety of enhanced or modified confections. An example confection which may be provided includes an edible substrate and at least one active ingredient provided to the edible substrate.

Figure 2:
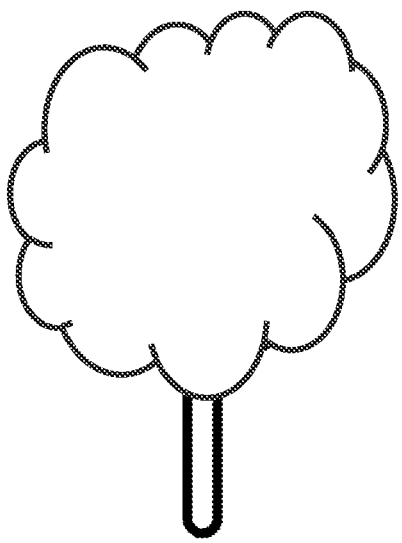
FIG. 2 schematically illustrates an example substrate without any active ingredients.
Figure 4:
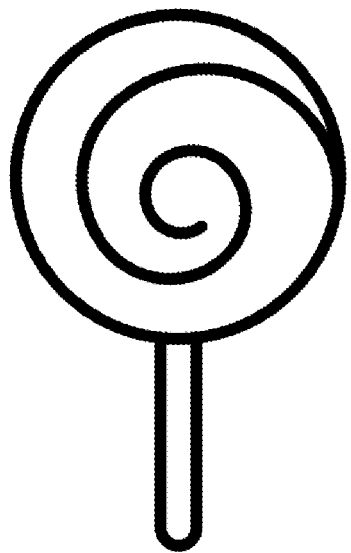
FIG. 4 schematically illustrates another example substrate without any active ingredients.
Figure 6:
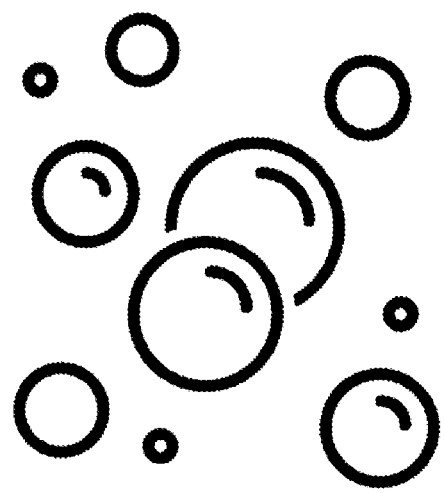
FIG. 6 schematically illustrates yet another example substrate without any active ingredients.

FIGS. 2, 4 & 6 schematically illustrate various example substrates suitable for use in association with disclosed methods. The example substates of FIGS. 2, 4 & 6 may be suitable to produce disclosed confections. The edible substrate may further include one or more components or ingredients which are soluble in water or otherwise water-sensitive. The edible substrate may further include at least one sugar such as sucrose, glucose or fructose. Additionally and/or alternatively, sorbitol, mannitol, xylitol and/or isomalt may be included. The edible substrate used in the confectionery method to produce a confection may be or may include a pastry, spun sugar (FIG. 2), a candy such as hard candy (FIG. 4), gum, breath mints and/or a popping candy (FIG. 6) such as that containing bubbles of carbon dioxide.

The at least one active ingredient may be configured for delivery to a user's bloodstream for pharmaceutical and/or recreational purposes. The at least one active ingredient may include but is not limited to nicotine, benzocaine, caffeine, taurine, natural and/or artificial flavors, fentanyl, methadone, MDA, MDMA, ketamine, psilocin, psilocybin, hemp extract, a *cannabis* distillate, a *cannabis* extract, delta-9-tetrahydrocannabinol, cannabidiol or cannabigerol.

Figure 3:
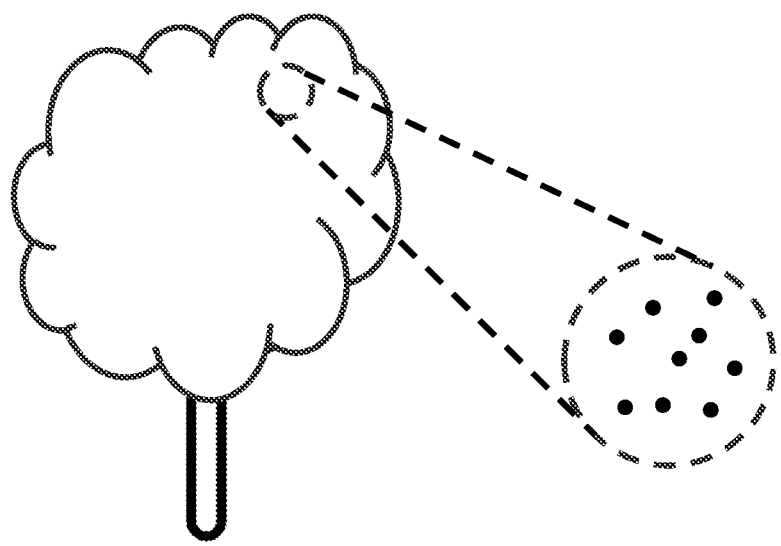
FIG. 3 schematically illustrates an example enhanced or modified confection with a detail view of an example active ingredient application.
Figure 5:
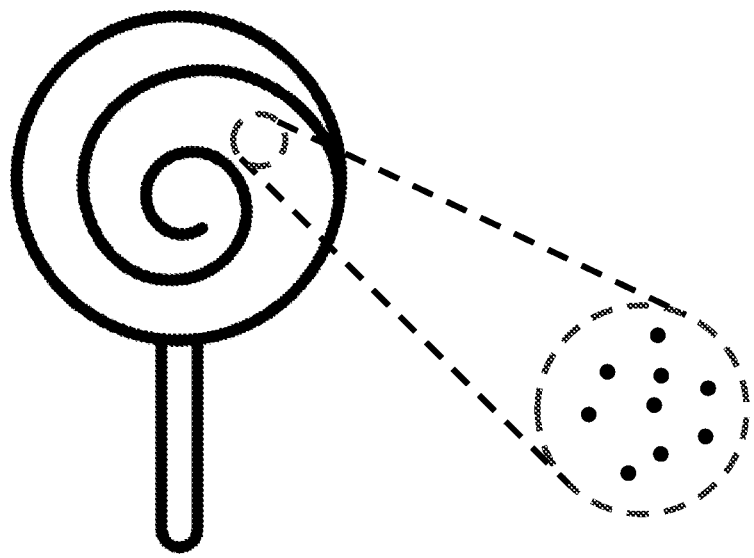
FIG. 5 schematically illustrates another example enhanced or modified confection with a detail view of an example active ingredient application.
Figure 7:
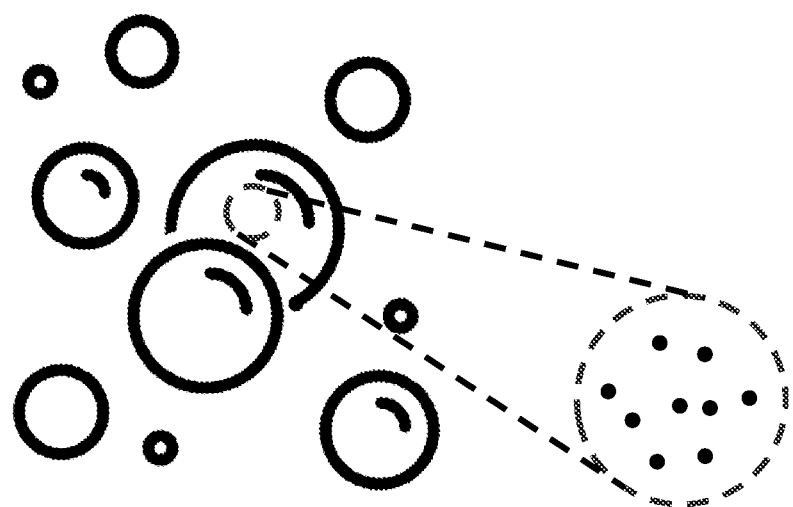
FIG. 7 schematically illustrates yet another example enhanced or modified confection with a detail view of an example active ingredient application.

FIGS. 3, 5 & 7 schematically illustrate various example modified or enhanced confections which may be produced by disclosed methods. It should be noted that active ingredients shown in FIGS. 3, 5 & 7 may not be visible to a consumer and/or may not be visible to the unaided eye. Further, active ingredients may exhibit a different distribution from that shown and/or may be present in higher or lower concentrations that suggested by FIGS. 3, 5 & 7.

While concentration of active ingredients in solution will be limited by solubility of the active ingredient in the selected vehicle, higher concentrations of solution will generally require less volume of vehicle be removed from the substrate after application of the solution.

The at least one active ingredient may be provided to the edible substrate superficially such that it coats as a thin film or microcrystals.

Embodiments of the disclosure are susceptible to being used for various purposes, including, though not limited to, enabling some users to prepare a confection with an active ingredient while enabling other users to ingest an active ingredient resulting from such preparation. Ingestion of the active ingredients may result in pharmaceutically, therapeutically and/or recreationally relevant effects. Similarly, embodiments could apply for any ingredient to be dosed to another substrate in a reproducible fashion, and where the vehicle is preferably non-toxic or easily evaporated. Further, embodiments may enable preparation of topical active ingredients for products such as bath bombs.

Example 1

111 milligrams of a 90% delta-9-tetrahydrocannabinol (d9THC) distillate was dissolved into 778 milligrams of 200 proof ethanol with agitation and 50° C. heat to create a solution containing 11.25% d9THC by mass. A pipette was used to transfer 90 milligrams of the solution as droplets onto a single 9.5 gram serving of popping candy, depositing 10 milligrams of d9THC onto the surface of its grains. A 50° C. stream of warm air was used to evaporate the ethanol from the surface of the candy, leaving 10 milligrams of d9THC as a thin film on the surface of the grains of candy.

Example 2

550 milligrams of a broad spectrum cannabinoid distillate containing 69% CBD was dissolved into 1.65 grams of 200 proof ethanol under agitation to create a solution containing 17.25% CBD by mass. A pipette was used to transfer 90 milligrams of this solution as droplets onto a single 9.5 gram serving of popping candy, depositing 15 milligrams of CBD onto the surface of its grains. A stream of 50° C. air was blown across the surface of the candy to evaporate the ethanol, leaving the 15 milligrams of CBD as a thin film on the surface of the grains of candy.

Example 3

250 milligrams of benzocaine was dissolved into 1.75 grams of 200 proof ethanol under agitation to create a solution containing 12.5% benzocaine by mass. A spray bottle was used to deposit 100 milligrams of this solution as a fine mist onto the surface of spun sugar (cotton) candy. The candy was placed into a vacuum chamber and pumped below atmospheric pressure until the ethanol had completely evaporated, leaving 12.5 milligrams of benzocaine on the surface of fibers of the spun sugar candy.

Example 4

111 milligrams of a 90% delta-9-tetrahydrocannabinol (d9THC) distillate was dissolved into 778 milligrams of 200 proof ethanol with agitation and 50° C. heat to create a solution containing 11.25% d9THC by mass. A pipette was used to transfer 90 milligrams of the solution as droplets to the surface of spun sugar candy. A 50° C. stream of warm air was used to evaporate the ethanol from the surface of the candy, leaving 10 milligrams of d9THC as a thin film on the surface of fibers of the spun sugar candy.

Example 5

111 milligrams of a 90% delta-9-tetrahydrocannabinol (d9THC) distillate was dissolved into 778 milligrams of 200 proof ethanol with agitation and 50° C. heat to create a solution containing 11.25% d9THC by mass. A spray bottle was used to deposit 90 milligrams of this solution as a fine mist onto the surface of spun sugar (cotton) candy. The candy was placed into a vacuum chamber and pumped below atmospheric pressure until the ethanol had completely evaporated, leaving 10 milligrams of d9THC on the surface of fibers of the spun sugar candy.

Example 6

40 milligrams of nicotine was dissolved into 1.30 grams of 200 proof ethanol with agitation and 50° C. heat to create a solution containing 3% nicotine by mass. A pipette was used to transfer 134 milligrams of the solution as droplets onto a single 9.5 gram serving of popping candy, depositing 4 milligrams of nicotine onto the surface of its grains. A stream of warm air was blown across the surface of the candy to evaporate the ethanol, leaving the 4 milligrams of nicotine as a thin film on the surface of the grains of candy.

Modifications to embodiments of the disclosure described in the foregoing are possible without departing from the scope of the disclosure as defined by the accompanying claims. Expressions such as "including", "comprising", "incorporating", "consisting of", "have", "is" used to describe and claim the disclosure are intended to be construed in a non-exclusive manner, namely allowing for items, components or elements not explicitly described also to be present. Reference to the singular is also to be construed to relate to the plural.

What is claimed is:

1. A confectionery method, comprising:
    dissolving at least one active ingredient in a volatile vehicle to form a solution;
    applying the solution to a substrate; and
    evaporating the volatile vehicle to leave the at least one active ingredient applied to the substrate.

2. The method as set forth in claim 1, wherein dissolving the at least one active ingredient in the volatile vehicle further comprises dissolving the at least one active ingredient in an anhydrous, volatile vehicle.

3. The method as set forth in claim 1, wherein dissolving the at least one active ingredient in the volatile vehicle further comprises dissolving the at least one active ingredient in pure ethanol.

4. The method as set forth in claim 1, wherein applying the solution to the substrate further comprises applying the solution to a substrate including at least one water-sensitive component.

5. The method as set forth in claim 1, wherein dissolving the at least one active ingredient further comprises dissolving cannabidiol.

6. The method as set forth in claim 1, wherein dissolving the at least one active ingredient further comprises dissolving a cannabinoid.

7. The method as set forth in claim 1, wherein dissolving the at least one active ingredient further comprises dissolving at least one active ingredient configured for buccal delivery.

8. The method as set forth in claim 1, wherein dissolving the at least one active ingredient further comprises dissolving at least one active ingredient configured for sublingual delivery.

9. The method as set forth in claim 1, wherein applying the solution to the substrate further comprises applying to an edible substrate.

10. The method as set forth in claim 1, wherein applying the solution to the substrate further comprises depositing droplets of the solution onto the substrate.

11. The method as set forth in claim 1, wherein applying the solution to the substrate further comprises spraying the solution onto the substrate.

12. The method as set forth in claim 1, wherein applying the solution to the substrate further comprises immersing the substrate in the solution.

13. A confection resulting from the method set forth in claim 1.

14. A confection, comprising:
    an edible substrate; and
    at least one active ingredient applied to the edible substrate; and
    wherein, with the at least one active ingredient applied to the edible substrate, the confection excludes any vehicle, solvent or oil for the active ingredient.

15. The confection as set forth in claim 14, wherein the at least one active ingredient further comprises cannabidiol.

16. The confection as set forth in claim 14, wherein the at least one active ingredient further comprises a cannabinoid.

17. The confection as set forth in claim 14, wherein the edible substrate further comprises at least one component which is soluble in water.

18. The confection as set forth in claim 14, wherein the edible substrate further comprises at least one sugar.

19. The confection as set forth in claim 14, wherein the at least one active ingredient further comprises at least one active ingredient configured for buccal delivery.

20. The confection as set forth in claim 14, wherein the at least one active ingredient further comprises at least one active ingredient configured for sublingual delivery.

21. The confection as set forth in claim 14, wherein the at least one active ingredient is provided to the edible substrate as a thin film.

22. The confection as set forth in claim 14, wherein the at least one active ingredient is provided to the edible substrate as crystals.

23. A confectionery method, comprising:
- dissolving at least one active ingredient in a volatile vehicle to form a solution;
- applying the solution to a substrate; and
- removing the volatile vehicle to leave the at least one active ingredient applied to the substrate.

* * * * *